United States Patent
Breindel et al.

(12)
(10) Patent No.: US 6,409,809 B1
(45) Date of Patent: Jun. 25, 2002

(54) PIGMENTED COATINGS EXHIBITING REDUCED FADING

(75) Inventors: Kenneth Breindel, Lansdale; Samuel A. Firman, Ambler, both of PA (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/500,336

(22) Filed: Feb. 8, 2000

Related U.S. Application Data

(60) Provisional application No. 60/119,144, filed on Feb. 8, 1999.

(51) Int. Cl.$^7$ .................. A01N 43/647; A01N 37/34; C09D 5/00
(52) U.S. Cl. .................. 106/18.32; 424/405; 514/383; 514/520; 514/525
(58) Field of Search .................. 106/18.32; 424/405; 514/383, 520, 525

(56) References Cited

U.S. PATENT DOCUMENTS

| | | | |
|---|---|---|---|
| 3,290,353 A | 12/1966 | Battershell et al. | 558/419 |
| 3,652,637 A | 3/1972 | Bimber | 558/327 |
| 4,012,261 A | 3/1977 | Sidi et al. | 106/18.31 |
| 4,022,906 A | 5/1977 | Sidi et al. | 514/375 |
| 4,130,434 A | 12/1978 | Arbir | 106/18.33 |
| 4,552,885 A | 11/1985 | Gabriele et al. | 514/316 |
| 5,124,353 A | 6/1992 | Clough et al. | 514/510 |
| 5,139,773 A | 8/1992 | Tadros | 514/315 |
| H1400 H | 1/1995 | Culbreath et al. | 514/383 |
| 5,393,770 A * | 2/1995 | Grayson | 514/383 |
| 5,492,696 A | 2/1996 | Price et al. | 424/417 |
| 5,540,920 A | 7/1996 | Vinopal et al. | 424/405 |
| 5,651,976 A | 7/1997 | Price et al. | 424/409 |
| 5,716,628 A | 2/1998 | Vinopal et al. | 424/405 |
| 5,760,067 A | 6/1998 | Jautelat et al. | 514/383 |
| 5,824,145 A | 10/1998 | Marganski et al. | 106/442 |
| 5,834,006 A | 11/1998 | Smith et al. | 424/409 |
| 6,071,940 A * | 6/2000 | Brandes et al. | 514/383 |
| 6,096,769 A * | 8/2000 | Perlitz et al. | 514/361 |

OTHER PUBLICATIONS

Martens, C.R., "Pigments, Paints, Varnishes, Lacquers, and Printing Inks", Riegel s Handbook of Industrial Chemistry, Eighth Ed. 1983, pp. 787–803 (no month).

The Pesticide Manual, Ninth Ed. 1991, pp. 159–160, 215–216, 427, 470, 654, 785, and 804 (no month).

Kataria et al., "Interactions of Fungicide —Herbicide Combinations Against Plant Pathogens and Weeds," Chem Abstr. No. 115:66781 (1990) no month.

Laidler et al., "Flutriafol/ Chlorothalonil: Control of Septoria Tritici in Winter Wheat," Chem Abstr. No. 114:201606 (1990) no month.

Liu et al., Use of Nanoparticles for the Controlled Release of Biocides in Pressure—Treated Solid Wood, Chem. Abstr. No. 127:172551 (1997) no month.

* cited by examiner

*Primary Examiner*—Anthony Green
(74) *Attorney, Agent, or Firm*—John E. Drach

(57) ABSTRACT

A method for preventing the fading of pigmented coatings, especially water based acrylic paints, includes incorporating therein a biocide containing a mixture of from about 1% to about 99% by weight of a halogenated benzonitrile compound and from about 1% to about 99% by weight of a conazole compound.

22 Claims, No Drawings

PIGMENTED COATINGS EXHIBITING REDUCED FADING

CROSS-REFERENCE TO RELATED APPLICATIONS

This application claims priority to U.S. Provisional application Serial No. 60/119,144 filed Feb. 8, 1999.

BACKGROUND OF THE INVENTION

1. Field of the Invention

The present invention relates to pigmented coatings, especially paints containing halogenated benzonitrile fungicide, and to a method for making such coatings.

2. Background of the Related Art

Biocides have been useful in various coating and paint formulations, such house paints, to prevent the growth of microorganisms such as bacteria, mold, and mildew. However, certain biocides can produce photochemical reactions upon exposure to ultraviolet (UV) radiation. This poses a problem especially for water-based exterior house paints, which are exposed to sunlight.

Halogenated benzonitrile based biocides, such as chlorothalonil, are effective at suppressing the growth of fungi, but present a problem in colored paints in that they lead to fading upon exposure to UV radiation. The fading is believed to be related to degradation of the binder, which produces chalking. Although the chalking can occur in light as well as dark colored paints, it is especially noticeable with dark or deeply hued pigments such as black, blue, etc. This problem precludes the use of halogenated benzonitrile based biocides in such paints.

What is needed is a way to incorporate halogenated benzonitrile based biocides in paint while having reduced fading.

SUMMARY OF THE INVENTION

The pigmented coatings described herein include a binder, a pigment, and a biocide containing from about 1% to about 99% by weight of a halogenated benzonitrile compound and from about 1% to about 99% by weight of a conazole compound.

Pigmented coatings with the combination of a conazole compound and a halogenated benzonitrile compound surprisingly exhibit less fading than pigmented coatings with only one type of biocide.

DETAILED DESCRIPTION OF PREFERRED EMBODIMENT(S)

While the invention described herein may be used in conjunction with any type of coating material, it is especially useful for paints. In particular, the invention herein is especially useful for dark colored exterior paints such as used on houses. As used herein the term 'dark' shall refer to coatings having a reflectance of no more than about 25%.

As used herein the term 'acrylic' encompasses homopolymers and copolymers having unsubstituted or substituted acrylic moieties including acrylates, methacrylates, vinylacrylics, styrenated acrylics and the like.

A paint is a coating material including a solid pigment suspended in a liquid vehicle and which is applied to various surfaces. The pigment can be inorganic or organic. Inorganic pigments can be white or colored and can include, for example, titanium oxide, zinc oxide, chromium oxide, iron oxide, carbon black, and various combinations thereof. Organic pigments can include, for example, para-chlorinated nitroanilines, naphthol red, Hansa, benzidine, dinitroaniline orange, lithol, Persian orange, tartrazine, alizarine, indathrene, indigo blue, indigo maroon, phthalocyanine blue, phthalocyanine green, rhodamine, malachite green, methyl violet, and Victoria blue.

The vehicle typically includes a binder and, usually, a solvent or diluent such as water, mineral spirits, alcohols, ethers, ketones and esters. Various binders are known and commonly used such as alkyds, acrylics, vinyls, latex, and combinations thereof. Latex or emulsion paints typically use water as the diluent. The paint dries after application to the surface by evaporation of the diluent and/or hardening of the binder by chemical reaction. Other components may optionally also be incorporated into the paint formulation such as dispersing agents, defoamers, surfactants, driers, extenders, and the like.

The coating material herein includes, in addition to the pigment, binder, and other optional components, a biocide containing a blend of from about 1% to about 99% by weight of a halogenated benzonitrile compound and from about 1% to about 99% by weight of a conazole based compound, preferably from about 10% to about 90% by weight of the halogenated benzonitrile compound and from about 10% to about 90% by weight of the conazole compound, more preferably from about 20% to about 80% of the halogenated benzonitrile compound and from about 20% to about 80% of the conazole based fungicide, and most preferably about 40% to 60% of the halogenated benzonitrile compound and 40% to 60% of the conazole compound.

The halogenated benzonitrile preferably has the formula:

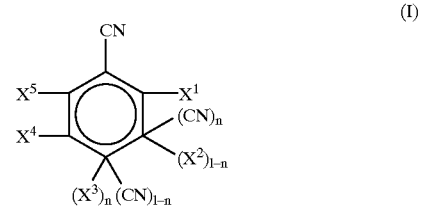

wherein $X^1$, $X^2$, $X^3$, $X^4$ and $X^5$ are hydrogen or halogen (Cl, F, Br, I) with at least one X being halogen, and n is equal to 0 or 1. A preferred di-cyano substituted halogenated benzene of formula (I) is tetrachloroisophthalonitrile, or 'chlorothalonil', which has the formula

The conazole compound has a molecular formula including at least one benzene ring and a heterocyclic group having the structure

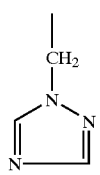

(III)

The conazole compound can optionally be selected from tetraconazole, tebuconazole, hexaconazole, cyproconazole, penconazole, and flutriafol.

The biocide described herein is preferably used in a water-based acrylic paint. An exemplary composition for such paint is described below.

More particularly, the pigment of the preferred paint composition includes particles of organic or inorganic pigment, the various types of which are well known in the art and examples of which have been set forth above. A suitable pigment includes titanium oxide ($TiO_2$) such as Ti-Pure® R-960 brand titania available from DuPont. Also useful are extenders such as Gold Bond® R brand silica ($SiO_2$), available from Gold Bond. Moreover, various colorants can be added to provide different hues to the pigment. Such colorants are known in the art.

Acrylic binder can be provided in the form of an acrylic emulsion such as Rhoplex® AC-264 acrylic emulsion, available from Rohm & Haas Corp.

Desirable additives include primary pigment dispersants (e.g., Nopcosperse® 100 brand anionic polyelectrolyte, available from Henkel Corp.), co-dispersants (e.g., Triton® CF-10 brand surfactant, available from Union Carbide), defoaming agents (e.g., Foamaster® VL defoamer, available from Henkel Corp.), antifreeze agents (e.g., ethylene glycol, propylene glycol), thickeners (e.g., Natrosol® MHR brand hydroxyethyl cellulose, available from Hercules), rheology modifiers (e.g., Attagel® 50 brand clay, available from Englehart Co.), coalescing agents (e.g., Texanol® brand high molecular weight alcohol type coalescing agent, available from Eastman Chemicals), and bactericides (e.g., Nuosept® 95 brand in-can preservative, available from Hüls-Degussa).

The following example is provided for the purpose of illustrating the present invention.

EXAMPLE

A paint composition was made by mixing the following ingredients in the following order:

| Ingredient | Amount |
|---|---|
| Deionized water | 450.0 parts by weight |
| Nopcosperse ® 100 (25%) | 18.0 parts by weight |
| Triton ® CF-10 | 7.2 parts by weight |
| Ethylene glycol | 126.0 parts by weight |
| Foamaster ® VL | 3.6 parts by weight |
| Natrosol ® MHR (2.5%) (mixed for 5 minutes) | 180.0 parts by weight |
| TiPure ® R-960 | 52.6 parts by weight |
| Gold Bond ® R silica (ground for 5 minutes) | 1256.8 parts by weight |
| Attagel ® 50 (added slowly and ground for 10–15 minutes) | 36.0 parts by weight |
| Rhoplex ® AC-264 | 1401.5 parts by weight |
| Foamaster ® VL | 10.8 parts by weight |
| Texanol ® | 10.8 parts by weight |
| Nuosept ® | 21.6 parts by weight |
| Natrosol ® 250 MH2 (2.5%) | 361.8 parts by weight |

To the above composition was then added Hüls Colortrend 'E' phthalocyanine blue colorant dispersion to an amount of about 12.5% by weight of the total paint composition.

An exposure test was conducted in two studies to determine the effect of weathering (UV exposure and/or condensation) on samples of panels with paints containing chlorothalonil, tetraconazole, and chlorothalonil/tetraconazole blend additives, respectively.

The panels were aluminum having a 3003 alloy mill finish. One coating (6 mils thick when wet) of the selected paint was applied to each panel and allowed to air dry for 7 days at ambient temperature.

Simulated weathering was performed by exposure of the panels to a QUV accelerated weathering tester providing UVA radiation at a power consumption of 1200 Watts (110 volts, 60 Hz). The exposure was conducted in alternating and repeating 6-hour cycles, one 6-hour cycle being an ultraviolet radiation exposure cycle (conducted at 80° C.), and the other cycle being a condensation cycle wherein the panels are exposed to moisture (conducted at 60°). The results are set forth below in Table I.

CIE La*b* System describes a color space wherein 'a' is the green(−)/yellow(+) axis. 'L' is lightness; 'C' is chroma or saturation.

TABLE I

| | Mildewcide | | OUV Weatherometer Exposure (6 hr. UV/6 hr. Condensation CIELa*b* System | |
|---|---|---|---|---|
| Panel # | (% as is) | Level | DL vs. Blank | DC vs. Blank |
| Study I (48 weeks) | | | | |
| 1 | Blank | 0.0 | NA | NA |
| 2 | Nopcocide N40D (40% CTL) | 2.0 | 5.52 (lighter) | −3.07 (less saturated) |
| 3 | TCZ/CTL (1:4) | 2.0 | −11.64 (darker) | 7.86 (more saturated) |
| 4 | TCZ | 2.0 | −2.20 | 1.02 |
| Study II (14 weeks) | | | | |
| 1 | Blank | 0.0 | NA | NA |
| 2 | Nopcocide N40D (40% CTL) | 4.0 | 2.89 | −1.47 |
| 3 | Nopcocide N40D (40% CTL) | 2.0 | 2.88 | −1.55 |
| 4 | N40D/TCZ | 4.0/0.4 | 0.81 | 0.69 |

CTL = Chlorothalonil
TCZ = Tetraconazole

The exposure tests show that the paints having the tetraconazole/chlorothalonil mixture (Panel 3, Study I) after 48 weeks of exposure had a darker color rating (i.e., −11.64) and more saturated color (7.86) than paints having comparable amounts of tetraconazole and chlorothalonil individually. Study II shows that as little as 0.4 parts tetraconazole in 4.0 parts chlorothalonil (i.e., 1:10 ratio) produces a significant improvement in the darkness and saturation retention of the paint as opposed to chlorothalonil alone.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A coating material containing:
   a binder, an amount of a pigment sufficient to provide a coating material having a reflectance of no more than about 25%, and an amount of a biocide effective for increasing the fading resistance of the coating material, the biocide containing a combination of from about 1% to about 99% by weight of a halogenated benzonitrile compound and from about 1% to about 99% by weight of a conazole compound.

2. The coating material of claim 1 wherein the halogenated benzonitrile compound has the formula:

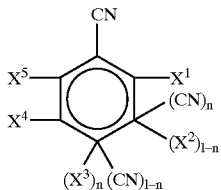

wherein $X^1$, $X^2$, $X^3$, $X^4$ and $X^5$ are each hydrogen or halogen with at least one X being halogen, and n is equal to 0 or 1.

3. The coating material of claim 2 wherein the halogenated benzonitrile compound is chlorothalonil.

4. The coating material of claim 1 wherein the conazole compound is selected from the group consisting of tetraconazole, tebuconazole, hexaconazole, cyproconazole, penconazole and flutriafol.

5. The coating material of claim 1 wherein the conazole compound is tetraconazole.

6. The coating of claim 1 further including water as a diluent, wherein the binder includes an acrylic or vinyl acrylic polymer.

7. The coating material of claim 6 wherein the halogenated benzonitrile compound is chlorothalonil, and the conazole compound is tetraconazole.

8. The coating material of claim 6 further including one or more additives selected from the group consisting of colorants, dispersants, defoaming agents, antifreeze, thickeners, rheology modifiers, coalescing agents and bactericides.

9. The coating material of claim 1 wherein the biocide contains a combination of from about 10% to about 90% by weight of the halogenated benzonitrile compound and from about 10% to about 90% of the conazole compound.

10. The coating material of claim 1 wherein the biocide contains a combination of from about 20% to about 80% by weight of the halogenated benzonitrile compound and from about 20% by weight to about 80% by weight of the conazole compound.

11. The coating material of claim 1 wherein the biocide contains from about 40% to about 60% by weight of the halogenated benzonitrile compound and from about 40% by weight to about 60% by weight of the conazole compound.

12. A method for preventing the fading of pigmented coatings, the method comprising:
   a) providing a pigmented coating material containing an amount of a pigment sufficient to provide a coating material having a reflectance of no more than about 25%, and a binder; and
   b) incorporating into the pigmented coating material an amount of a biocide effective for increasing the fading resistance of the coating material, the biocide containing a combination of from about 1% to about 99% by weight of a halogenated benzonitrile compound and from about 1% to about 99% by weight of a conazole compound.

13. The method of claim 12 wherein the halogenated benzonitrile compound has the formula:

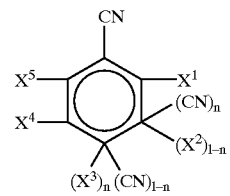

wherein $X^1$, $X^2$, $X^3$, $X^4$ and $X^5$ are each hydrogen or halogen with at least one X being halogen, and n is equal to 0 or 1.

14. The method of claim 13 wherein the halogenated benzonitrile compound is chlorothalonil.

15. The method of claim 12 wherein the conazole compound is selected from the group consisting of tetraconazole, tebuconazole, hexaconazole, cyproconazole, penconazole and flutriafol.

16. The method of claim 12 wherein the conazole compound is tetraconazole.

17. The method of claim 12 wherein the pigmented coating material includes water as a diluent and wherein the binder includes an acrylic polymer or vinyl acrylic polymer.

18. The method of claim 17 wherein the halogenated benzonitrile compound is chlorothalonil, and the conazole compound is tetraconazole.

19. The method of claim 17 wherein the pigmented coating material further includes one or more additives selected from the group consisting of colorants, dispersants, defoaming agents, antifreeze, thickeners, rheology modifiers, coalescing agents and bactericides.

20. The method of claim 12 wherein the biocide contains a combination of from about 10% to about 90% by weight of the halogenated benzonitrile compound and from about 10% to about 90% of the conazole compound.

21. The method of claim 12 wherein the biocide contains a combination of from about 20% to about 80% by weight of the halogenated benzonitrile compound and from about 20% by weight to about 80% by weight of the conazole compound.

22. The coating material of claim 12 wherein the biocide contains from about 40% to about 60% by weight of the halogenated benzonitrile compound and from about 40% by weight to about 60% by weight of the conazole compound.

* * * * *